United States Patent [19]
Osborn, III

[11] Patent Number: 6,010,001
[45] Date of Patent: *Jan. 4, 2000

[54] INDIVIDUAL PACKAGING FOR HYGIENIC WIPING

[75] Inventor: Thomas Ward Osborn, III, Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/975,792

[22] Filed: Nov. 21, 1997

Related U.S. Application Data

[63] Continuation-in-part of application No. 08/975,795, Nov. 21, 1997.

[51] Int. Cl.[7] ................................................ A61F 13/15
[52] U.S. Cl. ............................ 206/440; 206/438; 206/484
[58] Field of Search ............................... 206/204, 440, 206/438, 484–484.2, 363, 524.7, 570; 383/1, 200, 207; 604/385.1

[56] References Cited

U.S. PATENT DOCUMENTS

| | | |
|---|---|---|
| 2,917,049 | 12/1959 | Delaney . |
| 3,062,371 | 11/1962 | Patience . |
| 3,983,873 | 10/1976 | Hirschman . |
| 4,095,542 | 6/1978 | Hirschman . |
| 4,556,146 | 12/1985 | Swanson et al. ........................ 206/438 |
| 4,927,010 | 5/1990 | Kannankeril ............................ 206/204 |
| 4,984,907 | 1/1991 | Power ..................................... 206/204 |
| 5,431,970 | 7/1995 | Broun et al. ............................ 206/204 |

FOREIGN PATENT DOCUMENTS

| | | | |
|---|---|---|---|
| 4241845 | 9/1993 | Germany ................................ 206/204 |
| 1552810 | 9/1979 | United Kingdom ................... 206/204 |

Primary Examiner—Paul T. Sewell
Assistant Examiner—Luan K. Bui
Attorney, Agent, or Firm—Theodore P. Cummings; Jeffrey V. Bamber; Jacobus C. Rasser

[57] ABSTRACT

Individual packages to assist the hygienic insertion of an absorbent device into the interlabial space of a female user are disclosed. The individual package comprises a wrapper for packaging the absorbent device. The wrapper comprises a flexible sheet which is wrapped around the absorbent device. The flexible sheet has an absorbent inside surface adjacent to the absorbent interlabial device, which when the wrapper is opened, provides the user with a sanitary wiping device to wipe the labia while inserting said absorbent interlabial device into the interlabial space. In one embodiment, the wrapper is folded about the absorbent device relative to the longitudinal axis of the lower portion of the absorbent interlabial device forming a longitudinal fold, an opposing open end, and transverse side edges. The opposing open end and transverse side edges are sealed to form the individual package.

8 Claims, 3 Drawing Sheets

INDIVIDUAL PACKAGING FOR HYGIENIC WIPING

This is a continuation in part of the U.S. patent application Ser. No. 08/975,795, filed on Nov. 21, 1997, pending.

FIELD OF THE INVENTION

This invention relates to individual packages for absorbent devices that are worn interlabially by female wearers for catamenial purposes, incontinence protection, or both. More particularly, the present invention relates to individual packages to provide the user with a sanitary wiping device to wipe the labia while inserting the absorbent interlabial device into the interlabial space.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator," issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices that attempt to merge the structural features of the sanitary napkins and the tampons into a single device have also been proposed. Such hybrid devices are disclosed in U.S. Pat. No. 2,092,346, entitled "Catamenial Pad," issued to Arone on Sep. 7, 1937, and U.S. Pat. No. 3,905,372, entitled "Feminine Hygiene Protective Shield," issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad," issued to Jacks on Dec. 15, 1953, and U.S. Pat. No. 4,631,062, entitled "Labial Sanitary Pad," issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, and U.S. Pat. No. 4,595,392 issued to Johnson, et al. on Jun. 17, 1986. A commercially available interlabial device is FRESH 'N FIT® PADETTE® interlabial product that is marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

If the consumer needs only one interlabial pad for later use, the consumer must take precautions to protect the interlabial pad from soiling or contamination from the time it is removed from the box or bag until the article is used. This is a particular concern with respect to maintaining a sanitary environment during insertion and removal. That is, a need exists to hygienically store an individual interlabial pad while being transported to prevent transferring unsanitary particles to the interlabial space. Additional needs also exist for providing a hygienic and clean environment in and around the labial space.

The packaging for the commercially available FRESH 'N FIT® PADETTE® interlabial product is made from a coated paper sheet that is wrapped around the product and sealed on the transverse ends and along the longitudinal edges. The transverse ends and longitudinal edges of the product are sealed with an adhesive and are then crimped together. Another example of packaging for an interlabial pad is shown in U.S. Pat. No. 4,743,245 entitled "Labial Sanitary Pad" that issued to F. O. Lassen, et al. on May 10, 1988. However, there are drawbacks to these packages.

One important drawback is that these wrappers do not provide a means for users of interlabial products to preserve hygiene when inserting an interlabial device into the folds of the skin. The lack of hygiene in restrooms, the need to touch the doors of nonhygienic restrooms, and the necessity to touch themselves while inserting the device may result in the possibility of infection. In addition, when inserting the device during menstruation, it is desirable to keep the user's hands free from soiling. Therefore, the consumer needs an individual package that will protect the user's hand, fingers and the hygienic nature of the product.

Other packages for sanitary articles are described in U.S. Pat. No. 3,062,371 entitled "Internally Sterile Composite Package" that issued to D. Patience on Nov. 6, 1962 and U.S. Pat. No. 3,698,549 entitled "Packages for Small Articles" that issued to J. A. Glassman on Oct. 17, 1972. The Patience patent describes a package that is opened by folding back a panel from the package and removing its content by using sterile forceps. The Glassman patent describes a package that has internal pockets for holding flat articles such as gauze dressings or surgical sponges. The package is opened and exposes separate pockets for removal of individual articles.

Although the packages described in the Patience patent, the Glassman patent, the wrapper used with the PADETTE® product, and the wrapper described in the Lassen patent protect the enclosed article, the package or wrapper does not aid in the hygienic insertion and placement of the product or provide a barrier to prevent the wearer's hand from touching the product or the wearer's body.

Packages for tampons are described in U.S. Pat. No. 3,135,262 entitled "Tampon" that, issued to W. Kobler, et al. on Jun. 2, 1964 and U.S. Pat. No. 5,180,059 entitled "Package of a Sanitary Tampon" that issued to S. Shimatani and K. Shimatani on Jan. 19, 1993. The Kobler patent describes a wrapper that when unwrapped, forms what Kobler describes as an umbrella to cover the user's hands. Because of the shape of the tampon (the height of the tampon is considerably greater than the tampon's longitudinal dimension), the wrapper must be considerably longer than the tampon to encircle the user's hand when opened. When the wrapper is opened, the material that forms the shield is large and would be an impediment to proper placement. Additionally, the wrapper in the Kobler patent does not completely seal all parts of the product inside the package creating the potential for contamination. Specifically, the tear cord used to break the band that holds the wrapper onto the tampon must be touched by the user. The same cord, when the tampon is in use, then resides in the vaginal region that is sensitive to contamination.

The Shimatani patent describes a package that comprises packing sheets superimposed on another to enclose the tampon to create a shield when inserting the tampon. This patent fails to provide a sterile environment because it, too, does not seal all parts of the product inside the package that should be protected from contamination or prevent the user from touching parts that should maintain sterility. Additionally, the stiffness of the Shimatani package would not provide the user comfort when inserting the article.

The packages for the Kobler and Shimatani patents are tall and circular in shape. The Kobler and Shimatani packages may be suitable in packaging articles that have a height greater than its longitudinal dimension, however, with smaller articles such as an interlabial product where its longitudinal dimension is greater than the article's height, such a wrapper would not be feasible. The package of the present invention is flat in comparison and uses side panels to provide the user hygienic, comfortable insertion and placement of the interlabial device. Also, the package of the present invention differs from the Kobler and Shimatani packages because they are not flushable or biodegradable.

Therefore, it is an object of the present invention to provide a hygienic individual package for an interlabial device.

It is another object of the present invention to provide an individual package for an interlabial device that facilitates hygienic insertion of the device.

It is another object of the present invention to provide a hygienic individual package for an interlabial device that is flushable and biodegradable.

It is yet another object of the present invention to provide a sanitary wiping device to wipe the labia while inserting the absorbent interlabial device into the interlabial space.

These and other objects of the present invention will become more readily apparent when considered in reference to the following description and when taken in conjunction with the accompanying drawings.

SUMMARY OF THE INVENTION

This invention relates to individual packages for absorbent devices that are worn interlabially by female wearers for catarnenial purposes, incontinence protection, or both. More particularly, the present invention relates to individual packages that provide the user with a sanitary wiping device to wipe the labia while inserting the absorbent interlabial device into the interlabial space.

The individual package comprises a wrapper for packaging the absorbent interlabial device. The absorbent interlabial device has a width, a height and a longitudinal dimension that is greater than the height. The absorbent interlabial device is to be inserted at least partially within a user's interlabial space with the longitudinal dimension running lengthwise in the interlabial space. The wrapper comprises a flexible sheet that is wrapped around the absorbent interlabial device. The absorbent device has a longitudinal axis, an upper portion and a lower portion. The wrapper is preferably folded about the absorbent device relative to the longitudinal axis of the absorbent device forming a longitudinal fold, an opposing open end, and transverse side edges. In this preferred embodiment, the opposing open end and transverse side edges are sealed to form the individual package.

The flexible sheet has an absorbent inside surface adjacent to the absorbent interlabial device, which when the wrapper is opened, provides the user with a sanitary wiping device to wipe the labia while inserting said absorbent interlabial device into the interlabial space. The wrapper also protects the absorbent interlabial device during storage and transportation by shielding the interlabial device from contamination.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
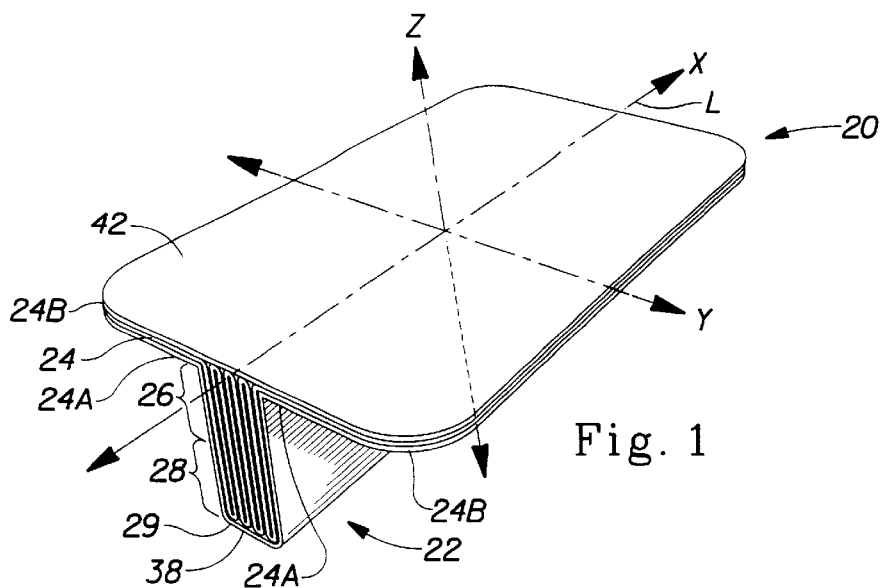
FIG. 1 is a perspective view of one embodiment of an absorbent interlabial device.

The present invention is directed to an individual package for an absorbent interlabial device. FIG. 1 shows one preferred embodiment of the absorbent interlabial device 20. The interlabial device, however, can be in many other forms, and is not limited to a structure having the particular configuration shown in the drawings.

As used herein, the term "absorbent interlabial device" refers to a structure that has at least some absorbent components, and is specifically configured to reside at least partially within the interlabial space of a female wearer during use. Preferably, more than half of the entire absorbent interlabial device 20 resides within such interlabial space, more preferably substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy that is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labial minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

The absorbent interlabial device 20 shown in FIG. 1 has a longitudinal centerline L that runs along the "x" axis shown in FIG. 1. The term "longitudinal," as used herein, refers to a line, dimension, axis or direction in the plane of the interlabial device 20 that is generally aligned with (e.g., approximately parallel to) a vertical plane that bisects a standing wearer into left and right body halves and extends between the front and rear of the wearer's body when the interlabial device 20 is worn. The terms "transverse" and "lateral" as used herein, are interchangeable, and refer to a line axis or direction that is generally perpendicular to the longitudinal direction (that is, in a direction outward from this vertical plane toward the wearer's thighs). The lateral direction is shown in FIG. 1 as the "y" axis. The "z" direction, shown in FIG. 1, is a direction parallel to the vertical plane described above. The term "upper" refers to an orientation in the z-direction toward the wearer's head. "Lower" or downwardly is toward the wearer's feet.

Figure 2:
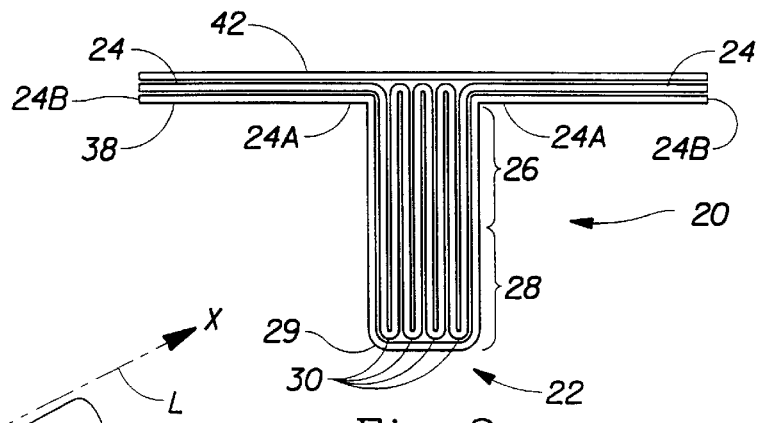
FIG. 2 is an end view of the absorbent device shown in FIG. 1.

In the embodiment shown in FIG. 1, the interlabial device 20 comprises a central absorbent portion (or "main absorbent") 22, and optionally, a pair of flexible extensions 24 joined to the central absorbent portion 22. The central absorbent portion 22 should be at least partially absorbent. The central absorbent portion 22 may comprise non-absorbent portions, such as a liquid impervious barrier to prevent absorbed exudates from leaking out of the central absorbent portion 22. The central absorbent portion 22 comprises an upper portion 26 and a lower portion 28 that is opposed to the upper portion. As shown in FIGS. 1 and 2, when the central absorbent portion 22 is of a uniform transverse dimension (i.e., there is no abrupt change in transverse dimension defining the juncture between the upper portion and lower portion) the division between the upper portion 26 and lower portion 28 is considered to be at a height equal to about one-half of the total height of the central absorbent portion 22. The flexible extensions 24 are joined to the upper portion 26 of the central absorbent portion. In use, the upper portion 26 is positioned furthest inward into the wearer's interlabial space. The lower portion 28 has a base (or "bottom edge" or "lower edge") 29.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

The size of the interlabial device 20 is also important to the comfort associated with wearing the device. In the embodiment shown in FIGS. 1, 2 and 3, the width of the central absorbent portion 22 of the interlabial device 20 as measured in the transverse direction (y-direction) is preferably between about 2 mm and less than or equal to about 12 mm, more preferably between about 3 mm and about 8 mm. In a preferred embodiment, the width of the central absorbent portion of the interlabial device 20 is about 4.5 mm. The central absorbent portion 22 of the interlabial device 20 has a length as measured along the longitudinal centerline, L, of between about 35 mm and about 120 mm. Preferably, the length of the interlabial device 20 is between about 45 mm and about 100 mm, and more preferably, is about 49 mm. The height (or "z"-direction dimension) of the central absorbent portion 22 is preferably between about 8 mm and about 35 mm, and more preferably is about 20 mm. Caliper measurements given herein were measured using an AMES gage with a 0.25 psi (gauge) load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psi (gauge).

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the central absorbent portion 22 thereof. The central absorbent portion 22 preferably has a capacity of at least about 1 g of 0.9% by weight saline solution, and may have a capacity of up to about 30 g by using absorbent gels or foams that expand when wet. Capacities may typically range from about 2 to about 10 grams, for saline. Those skilled in the art will recognize that the capacity for absorption of body exudates such as menses will typically be smaller than the capacities given above for absorption of saline. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

The central absorbent portion 22 of the interlabial device 20 may comprise any suitable type of absorbent structure that is capable of absorbing and/or retaining liquids (e.g. menses and/or urine). The central absorbent portion 22 may be manufactured in a wide variety of shapes. Non-limiting examples include ovoid, trapezoidal, rectangular, triangular, cylindrical, hemispherical or any combination of the above. The central absorbent portion 22 may, likewise, be manufactured and from a wide variety of liquid-absorbent materials commonly used in absorbent articles such as comminuted wood pulp that is generally referred to as airfelt. Examples of other suitable absorbent materials include cotton; creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. Preferred absorbent materials comprise folded tissues, woven materials, nonwoven webs, needle punched rayon, and thin layers of foam. The central absorbent portion 22 may comprise a single material or a combination of materials, such as a wrapping layer surrounding a central wadding comprised of a different absorbent material.

In the embodiment shown in FIGS. 1 and 2, the central absorbent portion 22 of the absorbent interlabial device 20 comprises a pleated structure. As shown in FIGS. 1 and 2, the central absorbent portion 22 comprises a folded tissue web. The folded tissue web preferably has a strength greater than that of standard non-wet strength toilet tissue. Preferably, the central absorbent portion 22 comprises a tissue having a temporary wet strength of greater than or equal to about 100 g. In a preferred embodiment, this wet strength will decay to about 50% or less of the original strength over about 30 minutes when measured under a wet burst strength test.

As shown in FIGS. 1 and 2, the tissue web comprising the central absorbent portion 22 is folded into a pleated structure comprising a plurality of pleats 30 that are arranged in a laterally side-by-side relationship. The tissue web can be folded so that it has any suitable number of pleats. Preferably, the tissue web is folded so that the overall caliper (i.e., the width) of the central absorbent portion 22 of this embodiment is between about 2 mm and less than or equal to about 8 mm.

The pleats in the folded tissue web are preferably connected or joined (or retained) in some suitable manner so that the pleated sections maintain their pleated configuration, and are not able to fully open. The pleats can be connected by a variety of means including the use of thread, adhesives, or heat sealing tissues which contain a thermoplastic material, such as, polyethylene. A preferred design uses stitching which joins all of the pleats in the central absorbent portion 22 together with cotton fiber. Preferably, the main absorbent structure 22 is provided with five stitch locations (four at the corners and one additional location approximately midway between the two lower corners).

The pleated structure of the central absorbent portion 22 provides several advantages. One advantage provided by the pleated structure is that exudates can penetrate into the pleats of the structure which present a larger and more effective absorbent surface for acquisition than a flat surface. This is particularly important when dealing with potentially viscous fluids and particulate material such as cellular debris and clots which can plug the surface of the structure presented to the body. A second advantage of this design is that the caliper (or width) of the product can be easily and conveniently controlled by varying the number of pleats. Another advantage of the pleated structure is that the number, thickness, and tightness of the pleats control the stiffness of the structure.

The stiffness of the central absorbent portion 22 is important for product comfort. If the central absorbent portion 22 is too flexible, the device is not conveniently or easily placed between the folds of the labia, if it is too stiff, the device is uncomfortable and when the user is in a sitting position, the product can be forced forward against the clitoris causing discomfort. The central absorbent portion 22 preferably has a stiffness approximately equal to that of the products described in U.S. Pat. Nos. 4,995,150 and 4,095,542.

Figure 3:
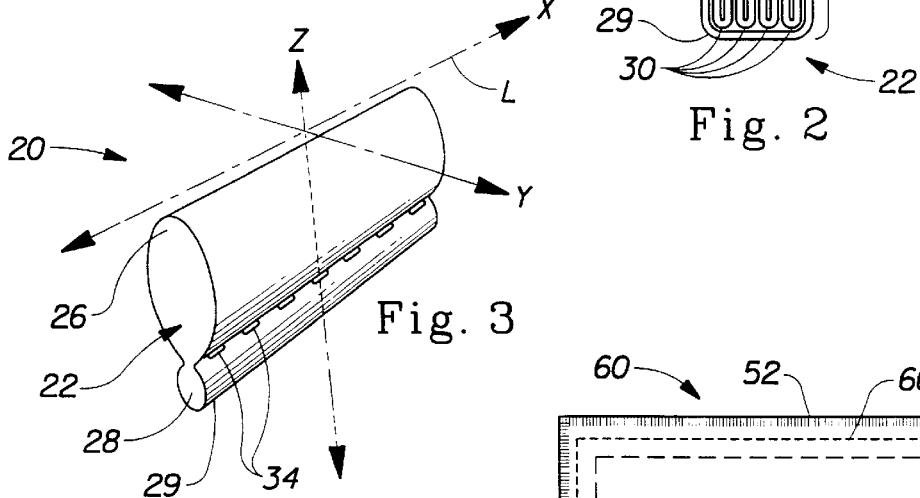
FIG. 3 is a perspective view of another embodiment of an absorbent interlabial device.

In the embodiment shown in FIG. 3, the central absorbent portion 22 is formed of a soft absorbent material such as rayon fibers or other suitable natural or synthetic fibers or sheeting. The central absorbent portion 22 shown in FIG. 3 is generally of an ovoid cross sectional shape. The central absorbent portion 22 of the embodiment shown in FIG. 3 comprises an upper portion 26 with a larger transverse sectional dimension relative to that of the lower portion 28. The upper portion 26 is preferably integral with the lower portion 28. In less preferred embodiments, however, the upper portion 26 and lower portion 28 may comprise separate elements joined together by any suitable means know in the art. In the embodiment shown in FIG. 3, the juncture of the upper portion 26 and lower portion 28 of the central absorbent portion 22 comprises a substantially abrupt change in the transverse dimension thereby forming a shoulder-like configuration at such juncture. In the embodiment shown in FIG. 3, the juncture of the upper portion 26 and lower portion 28 of the central absorbent portion 22 is formed by stitching 34.

In a variation of the embodiment described above and shown in FIG. 3, the upper portion 26 may have a smaller transverse sectional dimension relative to the transverse sectional dimension of the lower portion 28, and the portions may have different absorbent capacities. In other embodiments, such as that shown in FIGS. 1 and 2, the juncture between the upper portion 26 and the lower portion 28 can be indistinguishable.

The central absorbent portion 22 can be made by any suitable process. U.S. Pat. No. 4,995,150 issued to Gerstenberger et al. on Feb. 26, 1991 and U.S. Pat. No. 4,095,542 issued to Hirschman on Jun. 20, 1978 describe methods for making absorbent devices which are suitable for use as the central absorbent portion 22 of the absorbent interlabial device 20 shown in FIG. 3.

As shown in FIGS. 1 and 2, the absorbent interlabial device 20 preferably also comprises a pair of flexible extensions 24 which are joined to the upper portion 26 of the central absorbent portion 22 of the absorbent interlabial device 20. In the preferred embodiment shown in FIGS. 1 and 2, the flexible extensions 24 are generally rectangular in shape. Other shapes are also possible for the flexible extensions 24 such as semi-circular, trapezoidal, or triangular. The flexible extensions 24 preferably are from about 40 mm to about 160 mm in length, more preferably from about 45 mm to about 130 mm in length, and most preferably from about 50 mm to about 115 mm in length. While the flexible extensions 24 can have a length (measured in the x-direction) which is shorter than the central absorbent portion 22, preferably they have a length which is the same as or longer than the central absorbent portion 22 of the absorbent interlabial device 20. The width of each flexible extensions refers to the distance from the attachment of flexible extension 24 to the central absorbent portion 22 (or the proximal end 24A of the flexible extension 24) to the distal end (or free end) 24B of the flexible extension 24. The width of the flexible extensions 24 is preferably about equal to or greater than the height of the central absorbent portion as described above. The caliper of the flexible extensions is preferably less than or equal to about 3 mm, more preferably less than or equal to about 2 mm, and most preferably less than or equal to about 1 mm. Ideally, the caliper of the flexible extensions 24 and the central absorbent portion 22 are selected such that the caliper of the overall absorbent interlabial structure 20 is less than or equal to about 8 mm.

The flexible extensions 24 may be constructed of a tissue layer. A suitable tissue is an airlaid tissue available from Fort Howard Tissue Company of Green Bay, Wis., and having a basis weight of 35 lbs./3000 sq. ft. Another suitable airlaid tissue is available from Merfin Hygienic Products, Ltd., of Delta, British Columbia, Canada, having a basis weight of 61 g/m² and having the designation grade number 176. Still another suitable material is an airlaid cotton batt such as that sold as cosmetic squares by Revco Stores, Inc. of Twinsberg, Ohio. The flexible extensions 24 may optionally be backed with a layer of material which is impervious or semi-pervious to body exudates such as polyethylene, polypropylene, or a polyvinylalchohol.

In the embodiment shown in FIGS. 1 and 2, the pair of flexible extensions 24 may comprise a single sheet of material extending to either side of the longitudinal centerline L of the central absorbent portion 22 of the absorbent interlabial device 20. Alternatively, the pair of flexible extensions 24 may comprise separate sheets of material independently joined to the upper portion 26 of the central absorbent portion 22. Preferably, the flexible extensions 24 are arranged symmetrically about the longitudinal centerline L of the central absorbent portion 22. The flexible extensions 24 are joined to the upper portion 26 of the central absorbent portion 22 of the absorbent interlabial device 20. Most preferably, the flexible extensions are joined to the top surface of the upper portion 26 of the central absorbent portion 22, or within about 5 mm of the top surface of the central absorbent portion 22.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

As shown in FIGS. 1 and 2, the flexible extensions 24 are attached to the upper portion 26 of the central absorbent portion 22. The flexible extensions 24 extend downwardly and outwardly from the central absorbent portion 22 to a free end 24B which is unattached to the central absorbent portion. The flexible extensions 24 may be biased slightly outward from the central absorbent portion 22 so as to tend to keep the extensions 24 in contact with the inner surfaces of the labia when the absorbent interlabial device 20 is in place. Additionally, the naturally moist surfaces of the labia will have a tendency to adhere to the material comprising the flexible extensions 24 further tending to keep them in contact with the inner surfaces of the labia. Preferably, the flexible extensions 24 should be capable of motion from a position where the free ends of the flexible extensions 24 lie adjacent to the central absorbent portion 22 to a position where the flexible extensions 24 extend directly out from the central absorbent portion 22 in the transverse direction.

The flexible extensions 24 may be joined to the upper portion 26 of the central absorbent portion 22 by any variety of means. For example, in the embodiment shown in FIGS. 3, flexible extensions 24 may be joined to the upper portion 26 using any suitable adhesive centered about the longitudinal centerline L of the central absorbent portion 22 (i.e., on opposite sides of the longitudinal centerline L). The adhesive may extend continuously along the length of the central absorbent portion 22 or it may be applied in a "dotted" fashion at discrete intervals. Alternatively, the flexible extensions 24 may be joined to the upper portion 26 of the central absorbent portion 22 by stitching (such as with cotton or rayon thread), thermally bonding, fusion bonding, or any other suitable means known in the art for joining such materials.

The flexible extensions 24 should be of sufficient width and flexibility to allow the flexible extensions to cover the wearer's fingertips as the absorbent interlabial device 20 is inserted into the wearer's interlabial space. Additionally, the flexible extensions 24 should be capable of moving with the inner surfaces of the wearer's labia to maintain contact with the same. The flexible extensions 24 help keep the central absorbent portion 22 in place throughout a range of wearer motions such as squatting.

The flexible extensions 24 may be hydrophilic or hydrophobic. The flexible extensions 24 may be treated to make them less hydrophilic than the central absorbent portion 22. The hydrophilicity of a material is generally expressed in terms of its contact angle. Thus, the flexible extensions 24 may have an advancing contact angle greater than the advancing contact angle of the central absorbent portion 22, such that fluid is preferentially directed toward and absorbed by the central absorbent portion 22. The flexible extensions 24 may be either absorbent or non-absorbent. Preferably, the flexible extensions 24 have at least some absorbency. However, the majority of the fluid absorbed and retained by the absorbent interlabial device 20 will preferably ultimately be retained in the central absorbent portion 22. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The pleated design shown in FIGS. 1 and 2 has the additional benefit of easily providing the flexible extensions 24. The extensions 24 can comprise the same material as the central absorbent portion 22, or they can comprise a different material. The extensions 24 are joined to the upper portion 26 of the central absorbent portion 22, and most preferably, for this embodiment, are joined to the top surface of the central absorbent portion 22, or within 1 millimeter of the top surface of the central absorbent portion 22. Preferably, in the embodiment shown in FIGS. 1 and 2, the extensions 24 are integral portions of the central absorbent portion 22 (that is, the extensions 24 comprise integral extensions of the absorbent tissue material that is folded to form the central absorbent portion 22.

The interlabial device 20 in any of the embodiments shown in the drawings may comprise other optional components. For example, the interlabial device 20 may comprise a topsheet 42 positioned over and joined to all or a portion of the body facing surface of the device 20 and/or a backsheet 38 positioned over and joined to all or a portion of its back surface, including the flexible extensions 24. Preferably, if a topsheet 42 and/or a backsheet 38 is used, these components are joined to at least a portion of the central absorbent portion. In an alternative embodiment, the central absorbent portion could be at least partially wrapped by a topsheet 42.

If a topsheet is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet may be manufactured from a wide range of materials such as woven and nonwoven materials comprised of natural fibers (e.g., wood or cotton fibers), synthetic fibers (e.g., polymeric fibers such as polyester, rayon, polypropylene, or polyethylene fibers) or from a combination of natural and synthetic fibers. Other woven and nonwoven materials may include polymeric materials such as apertured formed thermoplastic films, apertured plastic films, and hydroformed thermoplastic films; porous foams; reticulated foams; reticulated thermoplastic films; and thermoplastic scrims.

The topsheet may comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. The preferred topsheet for the interlabial device is the formed film described in one or more of the above patents and marketed on sanitary napkins by The Procter & Gamble Company of Cincinnati, Ohio as the "DRI-WEAVE" topsheet.

If such a formed film is used in an interlabial device, the body surface of the formed film topsheet is preferably hydrophilic so as to help liquid to transfer through the topsheet faster than if the body surface was not hydrophilic so as to diminish the likelihood that menstrual fluid will flow off the topsheet rather than flowing into and being absorbed by the central absorbent portion 22. In a preferred embodiment, surfactant is incorporated into the polymeric materials of the formed film topsheet. Alternatively, the body surface of the topsheet can be made hydrophilic by treating it with a surfactant such as is described in U.S. Pat. No. 4,950,254 issued to Osborn.

If a backsheet is used, the backsheet 38 could be impervious or semi-pervious to liquids (e.g., menses and/or urine) and is preferably flexible. As used herein, the term "flexible" refers to materials which are compliant and will readily conform to the general shape and contours of the human body. The backsheet 38 prevents the exudates absorbed and contained in the central absorbent portion 22 from wetting articles which contact the absorbent interlabial device 20 such as the wearer's undergarments. The backsheet also assists the central absorbent portion 22 in preventing the wearer's body from being soiled by exudates. Additionally, use of the backsheet may provide an improved surface for the wearer to grasp between the fingers as the absorbent interlabial device 20 is inserted, or as the device is optionally removed with the fingers.

The backsheet 38 may comprise a woven or nonwoven material, polymeric films such as thermoplastic films of polyethylene or polypropylene, or composite materials such as a film-coated nonwoven material. Preferably, the backsheet 38 is a film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The backsheet may permit vapors to escape from the central absorbent portion 22 (i.e., breathable) while still preventing exudates from passing through the backsheet.

Figure 4:
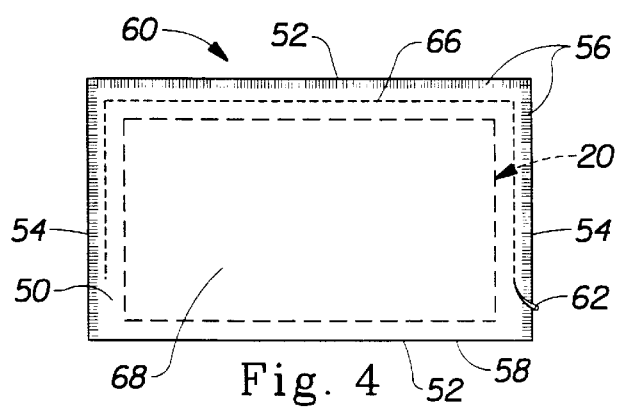
FIG. 4 is a side view of a preferred embodiment of the individual package of the present invention.

The embodiments shown in FIGS. 1–3 and any other variations of such a type of device may be packaged in an individual package 60 as shown in FIG. 4. The individual package 60 comprises a wrapper 50 that encloses the absorbent interlabial device 20 to provide a sanitary environment. The wrapper 50 should at least partially enclose the absorbent interlabial device 20, and preferably completely enclose the absorbent interlabial device 20. The wrapper 50 preferably comprises a rectangular sheet of flexible material. The wrapper 50 can be folded about or wrapped around the absorbent interlabial device 20 in any suitable manner. The wrapper 50 is preferably folded about or wrapped around the absorbent interlabial device 20 with its longer sides oriented perpendicular to the longitudinal centerline L of the absorbent interlabial device 20.

In the preferred embodiment shown, the wrapping of the wrapper 50 forms a longitudinal fold or bend 58 around the lower longitudinal edge 29 of the absorbent interlabial device 20, opposing longitudinal edges 52, side edges 54, and side panels 68. The upper longitudinal edge 52, that is, the longitudinal edge closest to the upper portion of the absorbent interlabial device 20, and the side edges 54 are sealed to form the individual package 60. The upper longitudinal edge 52 and side edges 54 are preferably frangibly sealed together forming crimped edges 56 to close off the sides and ends of the package. Suitable methods for frangibly sealing the edges of a package are described in U.S. Pat. No. 4,556,146 issued to Swanson, et al., U.S. Pat. No. 5,181,610 issued to Quick, and U.S. Pat. No. 5,462,166 issued to Minton, et al.

The individual package 60 preferably has a line of weakness which can be in the form of perforations 66 that are positioned along the upper longitudinal edge 52 and extend substantially along each side edge 54 of the package. In other alternate embodiments, the line of weakness can be in the form of a score line, such as that made by laser scoring. The individual package 60 preferably also has a tear strip or string 62 that generally extends along and in the direction of the perforations 66. The individual package 60 is opened by using the tear string 62 to break the perforations 66 along a significant portion of the periphery of the individual package 60. This releases two distinct side panels 68 which will drape over both sides of the user's fingers, and exposes the absorbent interlabial device 20.

Figure 5:
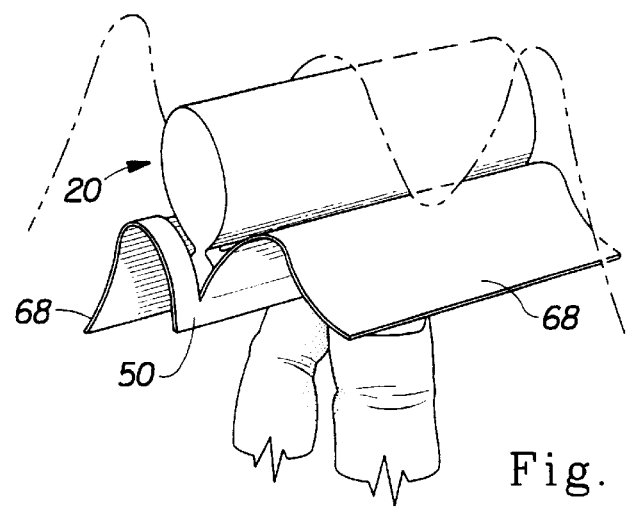
FIG. 5 is a perspective view of a wearer's body surrounding and including the wearer's labia majora and labia minora showing how the present invention is used to protect the user's fingers.

The wrapper 50 is partially removable from around the device 20 and the portion of the wrapper 50 forming the longitudinal fold or bend 58 remains between the user's hand and the absorbent device 20 to assist in the positioning and placement of the device 20. This configuration assists the user in positioning and placing the device 20, shields the user's fingers from being soiled, and keeps the user's fingers from touching the device 20 to maintain a sterile environment. FIG. 5 shows an opened individual package 60, as described above, with the interlabial device 20 being properly positioned in the folds of the labia.

Figure 6:
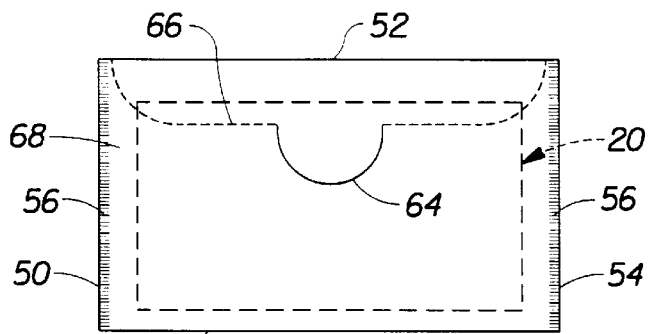
FIG. 6 is a side view of an alternative preferred embodiment of the present invention showing a front tab for opening the package.
Figure 8:
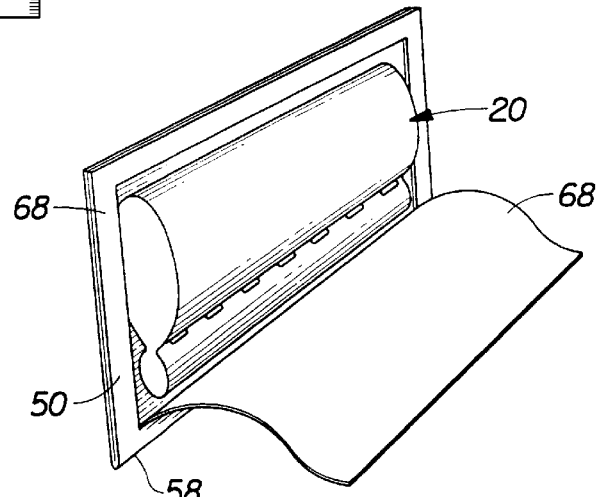
FIG. 8 is a perspective view of a partially opened package of the present invention.

In an alternative embodiment shown in FIG. 6, the individual package 60 is provided with a tab 64 instead of a tear string. The individual package 60 is opened by lifting the tab 64 and breaking the perforations 66 that are positioned along the upper portion of at least one side panel 68, that is closest to the upper portion of the absorbent interlabial device 20, to create an opening for the interlabial device 20. The crimped edges 56 are pulled apart to release the side panels 68. The tab 64 is formed when an extension of the upper longitudinal edge 52 is folded over or bent over onto a side panel 68. The side edges 54 are sealed as described above. In yet another alternative embodiment, the wrapper 50 of any of the embodiments described herein can be formed with two separate sheets that are frangibly sealed around the periphery of the sheets to form an individual package.

Figure 7:
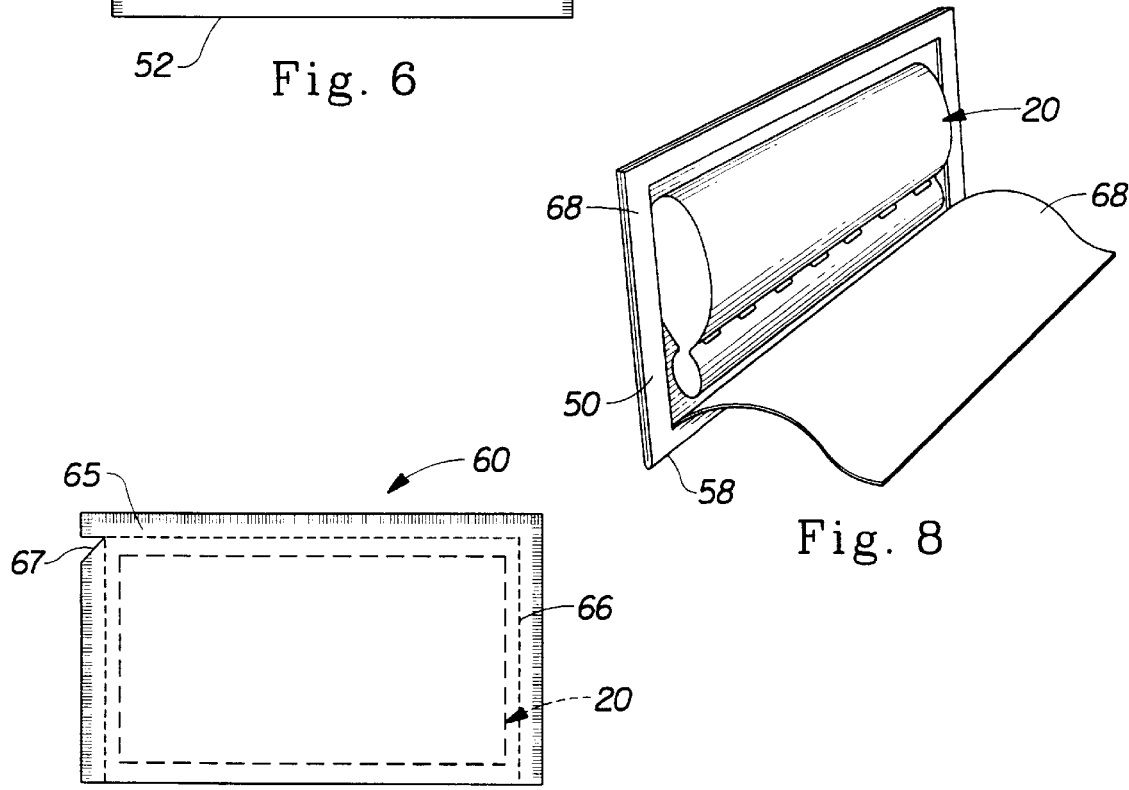
FIG. 7 is a side view of an alternative preferred embodiment of the present invention showing a side tab for opening the package.

In an alternative embodiment shown in FIG. 7, the individual package 60 is provided with a side opening feature, such as a side tab 65 instead of a tear string. The side tab 65 preferably aligns with perforations 66 along the upper longitudinal edge of the package. The individual package 60 is opened by peeling back the side tab 65 and breaking the perforations 66 that are positioned along the upper longitudinal edge 52 to expose the upper portion of the interlabial device 20. The crimped edges 56 are pulled apart to release the side panels 68. The package shown in FIG. 7 is otherwise similar to the package in FIG. 4 as described above. The side tab 65 may be formed in a number of ways, one of which removes material to form the side tab 65 after the package has been sealed by cutting the desired pattern of the side tab 65. For example a notch 67 can be cut into the side edge 54 of the package to form the side tab 65. Another way to form the tab would be to precut the wrapper material prior to forming the individual package.

The absorbent interlabial devices 20 shown in FIGS. 1–3 provide a convenient zone for grasping the product and inserting the interlabial device 20 into the space between the labia. The lower portion 28 of the central absorbent portion 22 can be grasped by the user, and held as the wrapper 50 is opened as described above. As shown in FIG. 5, the wrapper 50 is still in contact with the interlabial device 20, as the user places the interlabial device 20 into the space between the labia. Preferably, the wrapper 50 remains in contact with the interlabial device 20 until the device 20 is at least partially placed into the space between the labia for use. The wrapper 50 is then preferably removed.

An advantage of the present invention, as shown in FIG. 5, is that it protects the user's fingers from touching either the interlabial device 20 or her body at the point of insertion during insertion. The side panels 68 drape completely over both sides of the user's fingers to maintain a hygienic environment for inserting and placing the product. Another advantage of present invention is that it provides a protective covering for the interlabial device 20 during transport or storage of the product. Maintaining a hygienic environment for the interlabial device before and during use is vital to prevent transferring unsanitary particles to the interlabial space.

Alternatively, the embodiment shown in FIG. 7 can have perforations that are longitudinally positioned midway between the upper and lower longitudinal edges 52, and are located on both sides of the individual package. To open the package, the user would peel back and remove the upper portion of the wrapper and use the lower portion of the wrapper to grasp the lower portion 28 of the central absorbent portion 22. The wrapper would remain between the user's hand and the absorbent device 20, assist the user in positioning and placing the device 20, and keep the user's fingers from touching the device 20 to maintain a sterile environment.

Preferably, the wrapper 50 has a thickness of from about 0.0127 mm (0.5 mil) to about 0.127 mm (5.0 mils). The wrapper 50 may be made from plastic films, that may be thermoplastic, nonwoven materials, collagen films, paper tissues, or laminates of tissue and a film, nonwoven material and a film, or any of the foregoing types of material with a coating thereon. One embodiment of the present invention may be made from a low basis weight tissue that disintegrates in water. The low basis weight tissue can be made of carboxymethyl cellulose with wood pulp fibers and will disintegrate in water with a temperature of 75° F. (24° C.) in approximately 6 seconds; and disintegrate in water with a temperature of 50° F. in approximately 8 seconds. One such material is sold as DISSOLVO® WLD-35 water soluble purge dam material for gas-tungsten arc (TIG) welding by CMS Gilbreath Packaging Systems of Bensalem, Pa.

In addition, such low basis weight tissues may be combined with coatings or films like polyvinyl acetate (PVA), polyvinyl alcohol (PVOH), or methyl hydroxy propyl cellulose (MHPC) that also dissolve in water. One such material is sold as Mono-Sol® MC-8630 water soluble film by Chris Craft® Industrial Products, Inc., Gary, Ind. One preferred laminate material is made using a Hot Roll Laminator obtained from ChemInstruments by combining a 0.089 mm (3.5 mil) thick sheet of DISSOLVO® WLD-35 tissue with a 0.038 mm (1.5 mil) Mono-Sol® MC-8630 MHPC water soluble film. Laminating the tissue at a temperature between 344° F. (173° C.) to 366° F. (185° C.) and at a feed rate between 35 ft/min to 50 ft/min with the MHPC film produces a material 0.1 mm (4 mil) thick that is preferred for making the wrapper of the present invention.

The laminated material has a basis weight of 93.6 g/m$^2$. The material will disintegrate in water with a temperature of 75° F. (24° C.) in approximately 6.1 seconds and 7.9 seconds in water with a temperature of 50° F. The average time for the laminated material to dissolve is approximately 17.3 seconds in water with a temperature 75° F. (24° C.) and 34.4 seconds in water with a temperature 50° F. (10° C.).

The tear resistance (tear strength) of the film is alone is approximately 1575 gf, while the tear resistance of the DISSOLVO® WLD-35 is approximately 25 $g_f$ in the direction of the process flow through a manufacturing line for making the paper, the machine direction (MD), and 25 $g_f$ in the direction perpendicular to the machine direction, the cross-machine direction (CD). The tear resistance of the laminated material is approximately 88 $g_f$ (MD), and 76.8 $g_f$ (CD). The tear strength of the laminate is significantly less than that of the film by itself. The increase in the tear strength when comparing the paper to the laminated material provides a stronger package that will not tear as easily as paper alone. The reduction in tear strength when comparing the film to the laminated paper and film enables the user to open the package with greater ease than if the package were made from the film alone. When the materials are laminated, the superior tear resistant properties of the film are compromised, yet the strength of the paper is significantly increased, providing an ideal package that is easily opened, yet strong enough to resist tearing from handling and transporting.

The laminated material, like a number of the other wrapper materials identified above, also aids in heat sealing the package, provides a sanitary and moisture-free environment, and reduces noise associated with tearing paper when opening and carrying the package. The laminated material also produces a wrapper that can be opened with or without a line of weakness.

The coated side of the paper can either face the product or serve as the outer portion of the wrapper that is touched by the user. The coated side can be placed adjacent to the interlabial device 20 to protect against moisture. When the coating is applied or laminated to the wrapper material as a continuous film it forms a nonporous, impervious barrier that blocks moisture. However, placing the non-coated side of the wrapper 50 adjacent to the interlabial device 20 provides an absorbent surface on the inside surface of the side panels 68, that when the product is opened, can be used to absorb and wipe away discharge that may be found on the labia or interlabial space when inserting the interlabial device 20.

The wrapper 50 is preferably consrtructed of material that aids in providing comfort during insertion. The laminated material, like a number of the other wrapper materials identified above, provides a softer wrapper material. The wrapper 50 is preferably constructed of materials which are at least 70% biodegradable, more preferably at least 90% biodegradable, and/or which will fragment in water with agitation (as in a toilet). Preferably, the absorbent interlabial device 20 and the wrapper 50 for the absorbent interlabial device are both flushable separately or in combination, and when flushed the wrapper or the combination of the absorbent interlabial product and the wrapper will clear the toilet 80% of the time and biodegrade at least 95% of the time in a 28 Day Sludge Test. As used herein the terms "flushable and flushability" refer to a an article's ability to pass through typical commercially available U.S. household toilets and plumbing drainage systems without causing clogging or similar problems that can be directly associated with the physical structure of the article.

It is recognized, however, that there can be many differences between the various types of toilets available. Therefore, for the purposes of the appended claims, a test to determine the flushability of a catamenial product, such as an interlabial device, or the wrapper of a catamenial product is set out in the TEST METHODS section of this specification.

In addition, numerous embodiments of the individual packages described herein are possible. For example, the package could be provided in other configurations while still performing the functions described herein. Further, the packaging materials described herein can be used with a variety of absorbent articles configured for the absorption of body fluids such as female or male incontinence products, tampons, or externally worn sanitary napkins where a hygienic environment is a paramount concern. For instance, the adhesive on sanitary napkins and/or the wing adhesive of winged sanitary napkins can be covered by cover strips made of such materials. Additionally, a wrapper that serves as an individual package for a sanitary napkin such as that described in U.S. Pat. No. 4,556,146 entitled "Individually Packaged Disposable Absorbent Article" which issued to Swanson et al. on Dec. 3, 1985 could be provided that is made of such a material and/or have an absorbent inside surface which serves as a sanitary wiping device.

TEST METHODS

Flushability

Overview

As noted above, the terms "flushable or flushability" refer to a article's capacity to pass through typical commercially available household toilets and plumbing drainage systems without causing clogging or similar problems that can be directly associated with the physical characteristics of the article. For the purpose of the appended claims, interlabial products and their wrappers are evaluated for flushability via relative ease of toilet bowl and trap evacuation and subsequent transport through a simulated plumbing system. The flushability of such an article should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of the interlabial product or wrapper with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions an article will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 9:
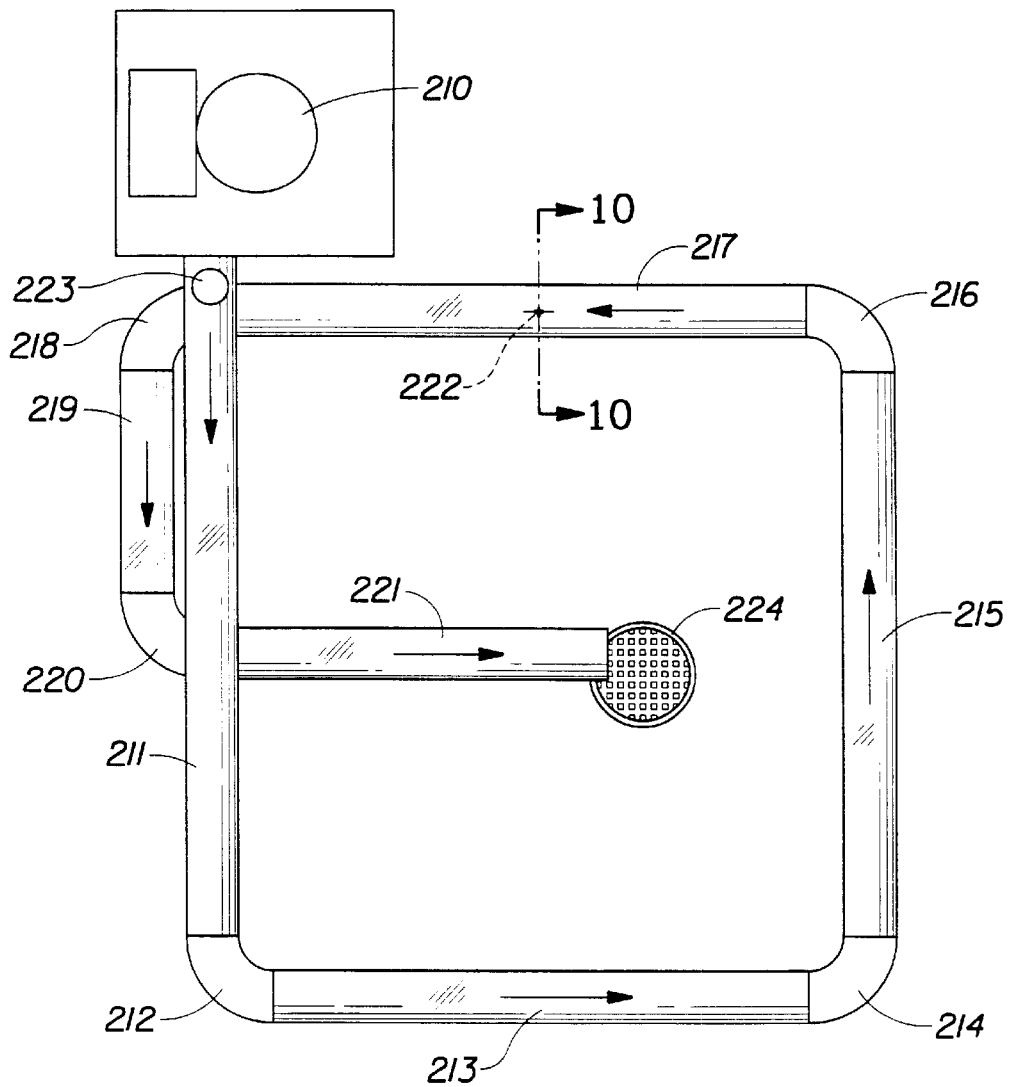
FIG. 9 is a top plan view of the apparatus suitable for the Flushability Test.
Figure 10:
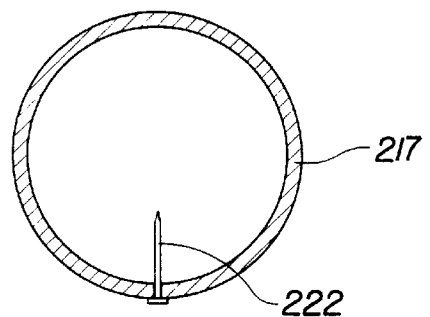
FIG. 10 is a cross sectional view of a portion of piping of the apparatus in FIG. 9.

An apparatus suitable for the flushability test is shown in plan view in FIG. 9. The apparatus includes:

a 3.5 gallon (13.2 liter) water saver siphon vortex toilet referred to as 210 (additional toilets can also be attached to the piping layout shown in FIG. 9 to evaluate the behavior of test samples using different flushing mechanisms such as commercial, pressure toilets);

approximately 59 feet (18 meters) of 4 inch (10 cm) inside diameter acrylic pipe (As can be seen from FIG. 9, the piping is assembled in roughly a square configuration having linear runs 211, 213, 215, 217, 219, 221 approximately 10 feet (3 meters) long);

a cast iron tee 223 slightly downstream of the toilet 210 that is open to the atmosphere for venting;

five cast iron ninety degree elbows 212, 214, 216, 218, and 220;

a spike or snag 222 positioned vertically (FIG. 10) approximately 15 feet from the pipe's terminal end and approximately 1 inch (2.5 cm) long; and a screen 224 (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: Standard CHARMIN® toilet tissue manufactured by The Procter & Gamble Company of Cincinnati, Ohio.

Synthetic Fecal Material: Prepared according to the method described below

Test Flushing Sequence

The test flushing sequence, consisting of two routines, simulates 2 days of normal toilet usage for a family of 4 (2 men, 2 women; based on consumer habits and practices research). The sequence of 40 total flushes consists of 14 flushes with an empty bowl; 8 flushes with tissue only; 6 flushes with tissue and wrapper; 6 flushes with tissue, interlabial product and wrapper; and 6 flushes with tissue and simulated fecal matter (SFM). When testing the wrapper and interlabial product as a combination, perform routines 1 and 2 using both the wrapper and the interlabial product placed individually into the bowl by first removing the product from the wrapper. The SFM, when it is used, is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips are placed in the bowl at 10 second intervals. Ten seconds after the final strip of tissue, the interlabial product or wrapper is placed into the bowl, the toilet is flushed. The flushing sequence is described below as a series of two routines combined in the following order:

Routine #1 (To be performed first 6 times for a total of 36 flushes)

1) Flush With Tissue Only—Take a drain line blockage reading 2 minutes after the water reaches the simulated obstruction, the snag point, wait 1 additional minute, and move to step 2.
2) Flush With Empty Bowl. Take a drain line blockage reading 2 minutes after the water reaches the snag point and move to step 3.
3) Flush With Tissue and Wrapper—Take a drain line blockage reading 2 minutes after the water reaches the snag point, wait 1 additional minute, and move to step 4.
4) Flush With Tissue and Interlabial Product and Wrapper—Take a drain line blockage reading 2 minutes after the water reaches the snag point, wait 1 additional minute, and move to step 5.
5) Flush With Empty Bowl. Take a drain line blockage reading 2 minutes after the water reaches the snag point and move to step 6.
6) Flush With Tissue and Simulated Fecal Matter (SFM). Take a drain line blockage reading 2 minutes after the water reaches the snag point, wait 1 additional minute.

Routine #2 (To be performed 1 time for a total of 4 flushes)

1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes for the sequence (Routine 1+Routine 2) is 40.

If, after the second flush in the flushing sequence, the product remains in the bowl or trap after flushing, the tissue and or catamenial product and or wrapper is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:

1) Incidence of failure (%) of wrapper to clear bowl and trap in one flush
2) Incidence of failure (%) of wrapper to clear bowl and trap in two flushes
3) Incidence of wrapper on simulated snag
4) Maximum level (%) of drain line blockage
5) Cumulative level (%) of drain line blockage over the 2 day simulated test period.

Preferably, the wrapper described herein will completely clear the bowl at least about 70% of the time in two or fewer flushes, more preferably at least about 80% of the time in one flush, and most preferably at least about 95% of the time in one flush. The wrapper described herein will preferably have a maximum level of drain line blockage of less than or equal to about 80%. The wrapper described herein will preferably have a cumulative level of drain line blockage over the 2 day simulated test period of less than or equal to about 50%.

Preparation of Synthetic Fecal Material

I. Materials Needed:

Feclone synthetic fecal matter (900 grams);
(Available from Siliclone Studio, Valley Forge, Pa. as product BFPS-7 dry concentrate)
Tap water at 100° C. (6066 grams)

II. Equipment Needed:

Mixer (Available from Hobart Corp., Troy, Ohio as Model A200)
Extruder (Available from Hobart Corp., Troy, Ohio as Model 4812)
Disposable Centrifuge tubes with screw caps (50 ml) (Available from VWR Scientific, Chicago, Ill. as Catalog No. 21-008-176)
Water Bath to control temperature to 37° C.

III. Preparation:

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C.

Water Dispersion Test

Apparatus

Stirrer Magnetic, Thermolyne type Model S7225 or 7200. Permanently inscribe a circle 3.5 inches (8.9 centimeter) on the top surface of the stirrer. The center of the circle must be coincident with the geometric center of the stirrer.
Stirring Bar 2.5 inch (6.2 centimeter) TEFLON coated with spinning ring. Permanently mark one end of the bar with black ink for a distance of 0.5 inch (1.2 centimeter) back from the tip.
Thermometer 30 to 120° F. with 1 degree divisions
Timer Digital stopwatch
Stroboscope Variable speed stroboscope, model 964 available from Strobette, Power Instrument, Inc. of Skokie, Ill. is suitable
Beaker Kimax brand 2000 milliliter with spout with a diameter at the base of 135±2 mm and a height at the 2000 ml mark of 162±2 mm, Inscribe a fill mark at a height of 5.6 inches (14.3 centimeters) from the flat bottom of the beaker. Do not use any beaker not having a flat bottom.

Conditioned Room Temperature and humidity should be controlled to remain within the following limits:

Temperature: 73±3° F. (23° C.±2° C.)

Humidity: 50±2% Relative Humidity

Test Setup

1. Fill the beaker to the fill mark with 73±3° F. (23° C.±2° C.) tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure

1. Hold a sample (e.g. an absorbent interlabial device or wrapper) 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch. If the sample disrupts the rotation of the stirring bar, stop the stirrer, re-orient the bar, and immediately start the stirrer again.
4. Record the time required until the sample separates into at least two pieces. Separation does not include the disassociation of a few individual fibers from an otherwise intact sample. The time is the total time the sample is immersed in the water including the time the stirrer may have been stopped to re-orient the sample.

A circular wire screen, consisting of an outer circle of 3" (7.62 cm) diameter and equally divided into 6 sections made from copper wire about 1 mm in diameter, may be placed immediately suspended above the stir bar in cases where the wrapper substantially disrupts the rotation of the stir bar.

If the wrapper repeatedly causes substantial disruption to the rotation of the stirring bar, the wrapper may be suspended by a string attached to the wrapper via a clamp attached to the wrapper ⅜" (.95 cm) from the edge of the wrapper, and then suspending the lowest end of the wrapper 1" above the stir bar.
5. Repeat steps 1 through 4 with an additional 3 samples.

Calculation and Reporting

Calculate and report the mean and standard deviation of the water dispersibility time for the four samples tested. Preferably, the wrapper will disperse into at least two fragments in less than or equal to about two hours.

Wet-Out Time

1. Hold the absorbent interlabial device or wrapper 3 to 4 inches (7.62 to 10.16 cm) above the surface of distilled water.
2. Gently drop the sample onto the water surface, so that the broad surface of the package strikes the surface.
3. Start timing when the sample is completely wet.
4. Repeat steps 1–2 for five samples.

Report a mean and standard deviation for the wet-out time. The wet-out time is preferably less than or equal to 30 seconds and more preferably less than or equal to 15 seconds.

28 Day Sludge Test

Purpose:

To determine the extent to which a wrapper disintegrates upon exposure to biologically active anaerobic sludge. Anaerobic conditions are typically found in household septic tanks, as well as in municipal sewage treatment facilities in the form of anaerobic sludge digesters. Test products, such as the wrapper are combined with anaerobic digester sludge to determine the extent and rate of disintegration of test products over a 28 day period. Disintegration (as measured by weight change) is typically measured on days 3, 7, 14, 21 and 28 of the particular study. This protocol is modeled after the National Sanitation Foundation, Ann Arbor, Mich., International Protocol: Evaluation of the Anaerobic Disintegration of a Test Product, November, 1992.

Materials:

Control Product

Tampax brand tampons will be used as a positive control product in the anaerobic disintegration test.

Material Preparation

Prior to the addition of the test and control products to the reactors, the materials will be dried in a hot air oven at 103°±2° C. for 2 hours and then weighed to determine the initial weight. Approximately equal weights of the control and test products will be placed in respective reactors.

Anaerobic Sludge:

The sludge used in this evaluation will be anaerobic sludge obtained from a municipal waste water treatment plant, or raw sewage obtained as influent from a waste water treatment plant that has been concentrated by settling and decanting the overlying water. Prior to use in the evaluation, the following parameters of the sludge will be measured in accordance with standard laboratory operating procedures:

Total solids

Total volatile solids pH

The sludge should meet the following criteria for use in the evaluation:

pH between 6.5 and 8

Total solids ≧ 15,000 mg/L

Total volatile solids ≧ 10,000 mg/L

The criteria for the activity of the sludge requires that the control tampon material must lose at least 95% of its initial dry weight after 28 days exposure.

Procedure:

The test and control products are added to a 2 L wide mouth glass flask (reactor) containing 1500 ml of anaerobic digester sludge or concentrated raw sewage. Three reactor flasks per test material per sampling day are prepared. Thus, if disintegration is measured on days 3, 7, 14, 21, and 28, there will be a total of 15 reactor flasks for the test product and 15 flasks for the control product. The reactors are sealed and placed in an incubator maintained at 35±2° C. On the specified sampling days, three reactors each for the test and control material are removed from the incubator. On the designated sample days, the contents of each reactor will be passed through a 1 mm mesh screen to recover any undisintegrated material. Any collected material will be rinsed with tap water, removed from the screen and placed in a hot air oven at 103±2° C. for at least 2 hours. The dried material will be weighed to determine final weight. Visual observations of the physical appearance of the materials when recovered from the reactors will also be made and recorded.

Results:

The rate and extent of anaerobic disintegration of each test material and the control material is determined from initial dry weights of the material and the dried weights of the material recovered on the sampling days. The percent anaerobic disintegration is determined using the following equation (percent weight loss):

$$\text{Percent Disintegration} = \frac{(\text{initial dry weight} - \text{final dry weight})}{(\text{initial dry weight})} \times 100$$

The average percent disintegration for the test and control products for each sampling day will be presented. For the purposes of the appended claims, the percent disintegration values are for day 28 of the study.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

I claim:

1. An individual package for an absorbent interlabial device, wherein said absorbent interlabial device is to be inserted at least partially within a user's interlabial space, said individual package comprising:

a wrapper for packaging said absorbent interlabial device, said wrapper comprising a flexible sheet which is at least partially wrapped around said absorbent interlabial device, said flexible sheet has an absorbent inside surface adjacent to said absorbent interlabial device, which when said wrapper is opened, provides the user with a sanitary wiping device to wipe the labia while inserting said absorbent interlabial device into the interlabial space.

2. The individual package of claim 1 wherein said wrapper comprises at least one of the materials selected from the group consisting of: tissue; collagen film; thermoplastic film; nonwoven material; laminates of thermoplastic film and tissue; laminates of collagen film and tissue; laminates of thermoplastic film and nonwoven material; and laminates of collagen film and thermoplastic film.

3. The individual package of claim 1 wherein said wrapper has an outside surface, and said outside surface is liquid impervious.

4. The individual package of claim 1 that is sufficiently flushable that it completely clears the bowl under the Flushability Test at least about 70% of the time in two or fewer flushes.

5. The individual package of claim 1 that is sufficiently flushable that it completely clears the bowl under the Flushability Test at least about 95% of the time in one flush.

6. The individual package of claim 1 wherein the time required for said wrapper to disperse into at least two fragments as measured by the Water Dispersion Test is less than about two hours.

7. The individual package of claim 1 wherein said wrapper causes drain blockage of less than 80%.

8. An individually packaged absorbent interlabial device comprising:

an interlabial device having a central absorbent portion comprising a longitudinal dimension, a width, a height, wherein said longitudinal dimension is greater than said height, an upper portion, and a lower portion thereof, said upper portion facing toward the vestibule floor of a female wearer during insertion into said female wearer's interlabial space and leading said lower portion during insertion therein, said upper portion having a longitudinal axis, said lower portion being opposed to said upper portion and upon insertion of said absorbent interlabial device into said interlabial space said lower portion facing away from the floor of the vestibule of said female wearer; and an individual package for said absorbent interlabial device comprising a flexible sheet which is folded about said absorbent interlabial device relative to said longitudinal axis of said lower portion forming a longitudinal fold, longitudinal edges, and transverse side edges wherein said longitudinal edges and said transverse side edges are sealed forming said individual package, which when said individual package is opened, provides the female wearer with a sanitary wiping device to wipe the labia while inserting said individually packaged absorbent interlabial device into said female wearer's interlabial space.

\* \* \* \* \*